US011723567B2

(12) United States Patent
Lin et al.

(10) Patent No.: US 11,723,567 B2
(45) Date of Patent: Aug. 15, 2023

(54) DEVICE, SYSTEM AND METHOD FOR EMOTION DETECTION

(71) Applicant: AmTRAN Technology Co., Ltd., New Taipei (TW)

(72) Inventors: Kao-Min Lin, New Taipei (TW); Yu-Hsaing Lin, New Taipei (TW)

(73) Assignee: AmTRAN Technology Co., Ltd., New Taipei (TW)

( * ) Notice: Subject to any disclaimer, the term of this patent is extended or adjusted under 35 U.S.C. 154(b) by 386 days.

(21) Appl. No.: 16/732,339

(22) Filed: Jan. 1, 2020

(65) Prior Publication Data

US 2020/0229748 A1 Jul. 23, 2020

(30) Foreign Application Priority Data

Jan. 22, 2019 (TW) .................................. 108102440

(51) Int. Cl.
*A61B 5/16* (2006.01)
*G06F 3/01* (2006.01)
(Continued)

(52) U.S. Cl.
CPC .............. *A61B 5/165* (2013.01); *A61B 5/369* (2021.01); *G06F 3/015* (2013.01); *G06F 17/142* (2013.01);
(Continued)

(58) Field of Classification Search
None
See application file for complete search history.

(56) References Cited

U.S. PATENT DOCUMENTS 6,254,536 B1 7/2001 Devito
6,292,688 B1 * 9/2001 Patton .................... A61B 5/378
600/545

(Continued)

FOREIGN PATENT DOCUMENTS

CN 109124624 A 1/2019
TW 201424687 A 7/2014

OTHER PUBLICATIONS

Islam, Monira, "Human Emotion Recognition using Frequency & Statistical Measures of EEG Signal", Aug. 1, 2013, IEEE Xplore, <URL: https://ieeexplore.ieee.org/abstract/document/6572658>, retrieved Nov. 23, 2022 (Year: 2013).*

*Primary Examiner* — Christopher J Fibbi
(74) *Attorney, Agent, or Firm* — CKC & Partners Co., LLC

(57) ABSTRACT

An emotion detecting device includes a memory, a processor and an output/input device. An emotion template with a plurality of emotional statuses is stored in the memory. The processor is configured to receive characteristic values transformed from brain waves of a pet and determine whether the brain waves correspond to a stable state based on variation of the characteristic values during a period. When it is determined that the brain waves correspond to the stable state, the processor determines whether the brain waves match some emotional status among the emotional statuses. When the brain waves match the emotional status, the output/input device outputs information regarding the pet being in the emotional status. When the brain waves do not match any of the emotional statuses in the emotion template, the processor updates the emotion template based on a confirm operation and the characteristic values.

10 Claims, 2 Drawing Sheets

(51) Int. Cl.
　　　*G06F 17/14*　　　(2006.01)
　　　*A61B 5/369*　　　(2021.01)
　　　*A61B 5/00*　　　(2006.01)
(52) U.S. Cl.
　　　CPC ....... *A61B 5/7257* (2013.01); *G06F 2203/011* (2013.01)

(56) References Cited

U.S. PATENT DOCUMENTS

| | | | | |
|---|---|---|---|---|
| 7,716,697 | B2* | 5/2010 | Morikawa | G06F 3/015 725/12 |
| 2007/0270668 | A1* | 11/2007 | Childre | A61B 5/16 600/300 |
| 2015/0199010 | A1* | 7/2015 | Coleman | A61B 5/0022 345/156 |
| 2017/0042439 | A1* | 2/2017 | Yeow | G16H 10/60 |
| 2018/0242904 | A1* | 8/2018 | Nakae | A61B 10/00 |
| 2019/0166434 | A1* | 5/2019 | Petley | H04R 25/505 |
| 2020/0214612 | A1* | 7/2020 | Liu | G06Q 30/0639 |

* cited by examiner

DEVICE, SYSTEM AND METHOD FOR EMOTION DETECTION

RELATED APPLICATION

This application claims priority to Taiwan Application Serial Number 108102440, filed Jan. 22, 2019, which is herein incorporated by reference in its entirety.

BACKGROUND

Technical Field

The present disclosure relates to a detecting device, a system for detection and a method for detection. More particularly, the present disclosure relates to a device and a system for detecting emotions of a pet and an operating method thereof.

Description of Related Art

It is a dream for every pet owner to be able to have zero distance communication with his/her pet. However, determining the current emotional status of a pet by the sounds it makes and its body movements is not sufficiently accurate. Moreover, since there are individual differences among the pet animals, the sounds and body languages of the pet animals may not be able to be generalized.

Accordingly, the current methods for determining emotions of pets obviously require further improvement for deficiency related to the issues described above.

SUMMARY

To address the issues described above, the present disclosure provides an emotion detecting device, an emotion detection system and a method for emotion detection.

One implementation aspect of the present disclosure is related to an emotion detecting device. The emotion detecting device comprises a memory, a processor, and an output/input device. The memory is configured for storing an emotion template with a plurality of emotional statuses. The processor is electrically coupled to the memory and the output/input device. The processor is configured for receiving a plurality of characteristic values transformed from a plurality of brain waves of a pet, and determining whether the brain waves correspond to a stable state based on variation of the characteristic values during a period. The brain waves are obtained by detection via a brainwave detecting device. When the brain waves correspond to the stable state, the processor determines whether the brain waves match a first emotional status of the plurality of emotional statuses. When the brain waves match the first emotional status, information regarding the pet being in the first emotional status is output at the output/input device. When the brain waves do not match at least one of the plurality of emotional statuses, the processor updates the emotion template in accordance with a confirmation operation and the plurality of characteristic values.

One further implementation aspect of the present disclosure involves an emotion detection system. The emotion detection system comprises a brainwave detecting device, a computing device, and an output/input device. The brainwave detecting device is configured for detecting a plurality of brain waves of a pet. The computing device is electrically coupled with the brainwave detecting device and the output/input device. The computing device transforms the brain waves to a plurality of characteristic values, and determines whether the brain waves correspond to a stable state based on variation of the characteristic values during a period. When the brain waves correspond to the stable state, the computing device determines whether the brain waves match a first emotional status among a plurality of emotional statuses of an emotion template. When the brain waves match the first emotional status, the pet is determined as in the first emotional status. When the characteristic values do not match at least one of the emotional statuses, the computing device updates the emotion template in accordance with a confirmation operation and the plurality of characteristic values. When the brain waves match the first emotional status, the output/input device outputs information regarding the pet being in the first emotional status.

One further implementation aspect of the present disclosure involves a method for emotion detection. The method for emotion detection comprises the following steps: receiving a plurality of characteristic values transformed from a plurality of brain waves of a pet, wherein the brain waves are obtained by detection via a brainwave detecting device; determining whether the brain waves correspond to a stable state based on variation of the characteristic values during a period; when the brain waves are determined as corresponding to the stable state, determining whether the brain waves match a first emotional status of a plurality of emotional statuses in an emotion template; when the brain waves match the first mood, outputting information regarding the pet being in the first mood; when the brain waves do not match at least one of the emotional status, updating the emotion template in accordance with a confirmation operation and the plurality of characteristic values.

Accordingly, based on the technical contents of the present disclosure, the embodiments of the present disclosure may provide improvements for the issue that it is difficult for users to understand the emotions of pets by providing an emotion detecting device, an emotion detection system, and a method for emotion detection.

DETAILED DESCRIPTION

The spirits of the present disclosure would be described by the figures and detailed description below. Having understood the embodiments of the present disclosure, one having ordinary skill in the art may certainly change and modify the teachings of the present disclosure without departing from the spirit and scope of the present disclosure.

The terms used herein are merely used for describing certain embodiments without limiting the present disclosure. Terms of single forms, such as "a," "an," "one," "this," "the," and "that" used herein, may similarly comprise those in plural forms.

The terms "first," "second," and the like are merely used for distinguishing components or operations which are described with identical technical terms, not for specifically designating an order or prioritized sequence thereof, nor for limiting the scope of the subject matter.

The term "coupled" or "connected" used herein may refer to two or more components or devices which are directly in physical contact with each other, or which are indirectly in physical contact; and the terms may also refer to two or more co-operating or acting components or devices.

The terms "comprising," "including," "having," "containing," etc. used herein are all open-ended terms, i.e. including but are not limited to what is described.

The term "and/or" used herein encompasses any single one or a combination of what is described.

Unless specifically noted, each of the terms used herein usually has the typical meanings of the term when used in the art, in the contents of the present disclosure and special contents. Some of the terms used for describing the subject matter may be discussed below or elsewhere in the Specification, in order to provide the skilled persons in the art with additional guidance for the description of the subject matter.

Figure 1:
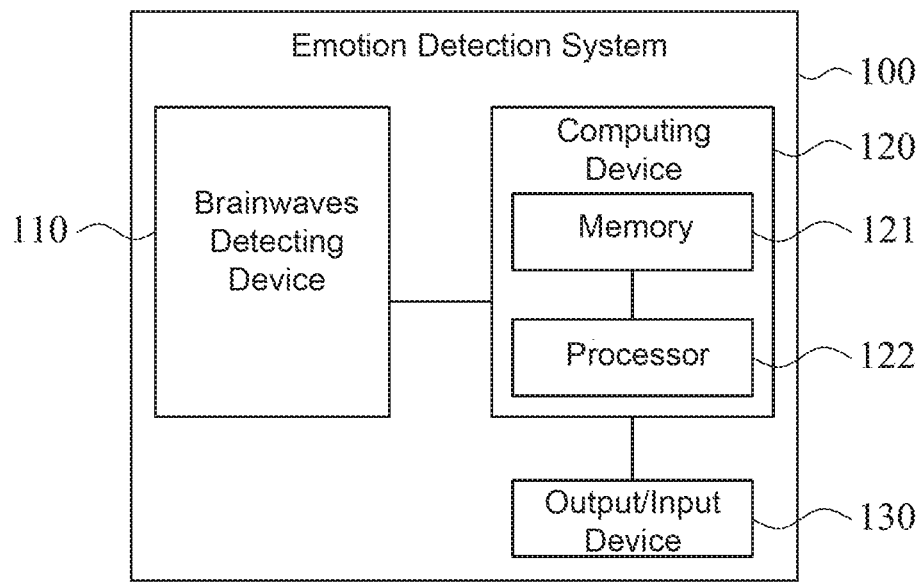
FIG. 1 is a schematic diagram illustrating an emotion detection system according to one embodiment of the present application.

FIG. 1 is a schematic diagram illustrating an emotion detection system 100 according to one embodiment of the present application. In some embodiments, the emotion detection system 100 comprises a brainwave detecting device 110, a computing device 120, and an output/input device 130, as shown in FIG. 1. In some embodiments, the computing device 120 comprises a memory 121 and a processor 122. The memory 121 is electrically coupled to the processor 122. In some embodiments, the computing device 120 may communicatively or electrically coupled with the brainwave detecting device 110 and the output/input device 130.

In some embodiments, the processor 122 may comprise, but is not limited to, a single processing unit or an assembly of multiple micro-processors which may be electrically coupled to the memory 121. In some embodiments, the memory 121 may be internal or external memory, including volatile or non-volatile memory. That is, the memory 121 may comprise non-transient computer-readable media.

In further embodiments, the processor 122 may be embodied by an application specific integrated circuit (ASIC). It is to be understood that the implementations described above for the processor 122 are merely exemplary and the subject matter is not limited as such. Other possible hardware components such as circuits and modules are all encompassed in the scope of the present disclosure.

In some embodiments, at least one instruction may be stored in the memory 121 for access and execution by the processor 122 to cause the processor 122 to implement an application process. In some embodiments, in addition to the at least one instruction, the data which is required for the processor 122 to execute the application process and which is generated after the processor 122 executing the application process may be further stored (or temporarily stored) in the memory 121.

In some embodiments, the memory 121 and the processor 122 are hardware components in a separate electronic device. For example, in some embodiments, the computing device 120 may be a smart phone, and the memory 121 and the processor 122 are components in the smart phone. For example, the computing device 120 may be a server while the memory 121 and the processor 122 are components in the server in some embodiments.

It is to be understood that the communicative or electrical coupling described above may refer to physical or non-physical coupling. For instance, the brainwave detecting device 110 may connect to the computing device 120 by wireless communication technology (Wi-Fi) in some embodiments, and the brainwave detecting device 110 and the computing device 120 may thereby conduct one-directional or bi-directional message exchange. Alternatively, the brainwave detecting device 110 may connect to the computing device 120 via physical wire connection in some embodiments. As such, the brainwave detecting device 110 and the computing device 120 may thereby conduct one-directional or bi-directional message exchange.

In some embodiments, the brainwave detecting device 110 comprises a wearable portion (not shown) adapted to a pet, such that the brainwave detecting device 110 may be disposed around the head of the pet. In some embodiments, the brainwave detecting device 110 has a respective microprocessor and potential detector which may detect the brain wave signals of the pet. In some embodiments, the brainwave detecting device 110 may further be used to filter out noise in the brain wave signals or to enhance partial signals in the brain wave signals. In some embodiments, the brainwave detecting device 110 has a respective memory in which the brain wave signals of the pet may be recorded. In some embodiments, the brainwave detecting device 110 may transmit messages corresponding to the brain wave signals of the pet to the computing device 120 autonomously or based on a request of the computing device 120.

It is to be understood that the pet may be of a relatively common type such as cats or dogs in some embodiments, but the subject matter is not limited as such.

In some embodiments, the output/input device 130 may comprise an output device (not shown) and an input device (not shown). In some embodiments, the output device may be a display or a speaker. In some embodiments, the input device may comprise a keyboard, a mouse or a touch display. In some embodiments, the output device may display messages from the computing device 120. In some embodiments, the input device may be configured to receive inputs from a user of the emotion detection system 100 and convert the inputs into messages to be transmitted to the computing device 120. In other words, the output/input device 130 is the communication medium between the computing device 120 and the user of the emotion detection system 100.

Figure 2:
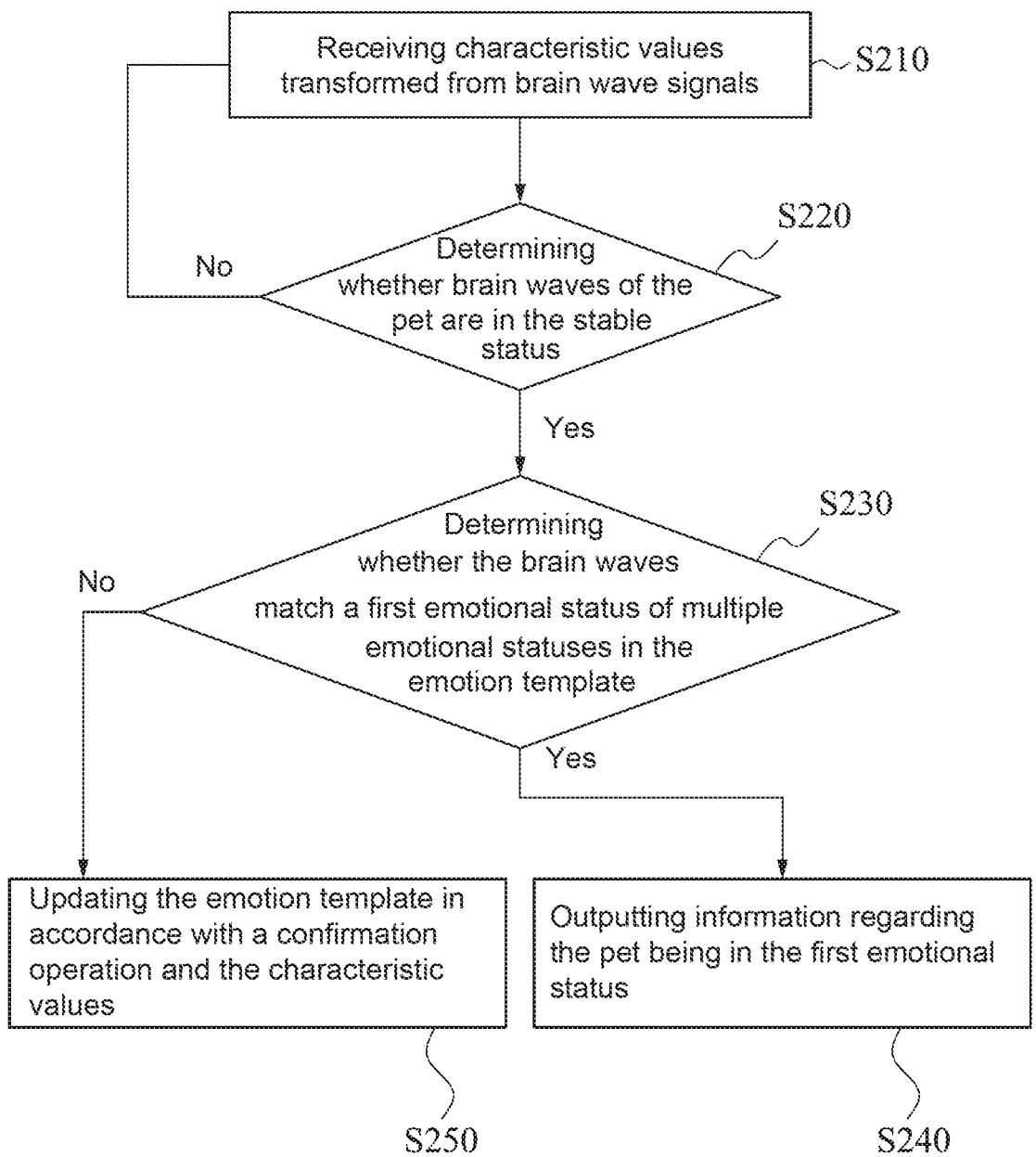
FIG. 2 is a flow diagram illustrating a method for emotion detection according to one embodiment of the present application.

FIG. 2 is a flow diagram illustrating steps of a method for emotion detection according to one embodiment of the present application. In some embodiments, a method 200 for emotion detection includes steps S210~S250. In some embodiments, the steps of the method 200 for emotion detection are implemented by the computing device 120 in the embodiment illustrated in FIG. 1, and specifically performed by the processor 122 in the computing device 120 which accesses the at least one instruction in the memory 121. Therefore, the implementing environment for the method 200 for emotion detection may be learnt by referring to the embodiment in FIG. 1. The steps S210-S250 in some embodiments would be described in details as below.

Step S210: receiving characteristic values transformed from the brain wave signals.

In some embodiments, the brainwave detecting device 110 may be disposed around the head of the pet to detect the brain wave signals of the pet. In some embodiments, the brainwave detecting device 110 may capture the brain wave signals of the pet periodically during a time period. For example, the brainwave detecting device 110 may capture the brain waves of the pet once per second and for a duration of 10 seconds. In other words, the brainwave detecting device 110 may capture the brain waves of the pet 10 times, and the time interval of the two captured pictures is one second. However, it should be noted that the period and the frequency for capturing brain waves in the present embodiment is merely one of the various implementations and the subject matter may not be limited as such.

In some embodiments, the brainwave detecting device 110 may autonomously transmit messages corresponding to the brain wave signals of the pet to the computing device 120, and the processor 122 in the computing device 120 may receive the messages corresponding to the brain wave signals of the pet so as to perform subsequent analysis.

In some embodiments, the brainwave detecting device 110 may record the messages corresponding to the brain wave signals of the pet. The processor 122 in the computing device 120 may autonomously access the messages corresponding to the brain wave signals from the memory in the brainwave detecting device 110 so as to perform subsequent analysis.

In some embodiments, while the brainwave detecting device 110 detects or records the brain wave signals of the pet, when the strength of the brain wave signals of the pet is determined as overly low, the brainwave detecting device 110 may send an alert signal to the computing device 120. The processor 122 in the computing device 120 may display the alert signal at the output/input device 130 to notify users of the emotion detection system 100. For example, when the brainwave detecting device 110 is disposed around the pet at an incorrect position or in an inappropriate manner resulting in a too low strength of the brain waves, the computing device 120 may output information regarding the low strength of the brain waves by the output/input device 130 to notify the user. The user may therefore adjust the disposed position of the brainwave detecting device 110. In some embodiments, the above described determination may be implemented by the processor 122 in the computing device 120.

In some embodiments, when the processor 122 obtains the messages corresponding to the brain wave signals of the pet, the processor 122 may transform those brain wave signals to a plurality of characteristic values. In some embodiments, the transformation of those brain wave signals to the plurality of characteristic values by the processor 122 is based on a transform algorithm. It is to be understood that the transform algorithm comprises at least one of a fast Fourier transformation (FFT) algorithm or a wavelet transformation algorithm in some embodiments, but the subject matter is not limited as such.

In some embodiments, the processor 122 may, based on the algorithm described above, transform each brain wave signal captured to a plurality (for example, a number N) of frequency data items. The plurality of frequency data items corresponding to the brain wave signals are the plurality of characteristic values described above, and these characteristic values may be considered as a separate characteristic set. Take a number N of frequencies for instance, each brain wave signal may be transformed into a row matrix (a1, a2, . . . , aN) which dimensions are N by 1. Each element of the matrix is a characteristic value respectively corresponding to one frequency. The number N therein is an integer greater than one (1).

In some embodiments, the transform algorithm described above may be performed by the brainwave detecting device 110, and the processor 122 in the computing device 120 may receive the characteristic values (i.e., multiple characteristic sets) transformed from these brain wave signals and further perform subsequent processing.

Step S220: determining whether the brain waves of the pet are in the stable state. When the brain wave signal is determined as corresponding to the stable state, go to the step S230. When it is not corresponding, return to the step S210.

In some embodiments, after the processor 122 obtains the characteristic values transformed from the brain wave signals, the processor 122 will determine whether the brain wave signals are approximately in a stable state based on variation of the characteristic values during a period.

It is to be understood that levels of activity of certain frequency ranges in the brain wave signals may correspond to a possible emotional status of the pet to a considerable extent in some embodiments. For example, the Gamma wave frequency range in 30 to 50 Hz indicates that the pet is in a status being sensitive to the environment, and the corresponding emotional status at such time may be being nervous or feeling unfamiliar and etc. For example, the Beta wave frequency range in 14 to 30 Hz indicates that the pet is in a status having more active thinking and being concentrate, and the corresponding emotional status at such time may be playful or feeling curious and etc. For example, the Alpha wave frequency range in 8 to 14 Hz indicates that the pet is in a more relaxed status, and the corresponding emotional status at such time may be happy or comfortable and etc. For example, the Theta wave frequency range in 4 to 8 Hz indicates that the pet is in a status feeling sleepy, and the corresponding emotional status at such time may be being tired or feeling exhausted and etc. For example, the Delta wave frequency range in 0.1 to 4 Hz indicates that the pet is in a deep sleeping status, and the corresponding emotional status at such time may be in a rest and etc. Accordingly, the processor 122 may determine the brainwave characteristic values for each frequency point to analyze the mood of the pet.

For example, the processor 122 may obtain multiple brain wave signals during a period and transform the multiple brain wave signals to a number K of brainwave characteristic sets in some embodiments. For instance, a first characteristic set is (a1, a2, . . . , aN). Wherein a1, a2, . . . , and aN are the characteristic values which are transformed from the first captured brain waves and respectively corresponding to each frequency point. The second to the Kth characteristic sets may be represented as (b1, b2, . . . , bN), (c1, c2, . . . , cN), . . . , and (k1, k2, . . . , kN). The processor 122 may calculate the variation of these k brainwave characteristic sets to determine whether the emotion of the pet is in a stable state during the period.

In some embodiments, the processor 122 may obtain k frequency data items during this period, each of which corresponds to each frequency point, to calculate a median for the k frequency data items corresponding to each frequency point. For example, a number k of frequency data items (a1, b1, c1, . . . , k1) corresponding to the first frequency point may be obtained, and a median m1 for the first frequency point may be calculated. Similarly, the processor 122 may obtain the frequency data items (ai, bi, ci, . . . , ki) corresponding to another frequency point (e.g., the i-th frequency point) and calculate the median mi for the frequency data items for this frequency point. Having obtained the medians for all of the frequency data items for all frequency points, a reference characteristic set (m1, m2, . . . mk) would be generated. Subsequently the brain waves corresponded by each characteristic set may be determined as in stable emotions or not based on a difference between the each characteristic set and the reference characteristic set.

In the present embodiment, whether the emotion of the pet is in a stable state may be determined based on the difference between each separate characteristic set and the reference characteristic set. For example, the processor 122 may calculate the frequency data items for each frequency point among the number k of brainwave characteristic sets and make a determination based on the frequency data difference with the reference characteristic set. When the difference is less than a predetermined threshold, a count is incremented. Whether the pet is in a stable emotion or not is determined based on the final count. For example, when the count is larger than a predetermined parameter, it is determined as in a stable emotional status. Otherwise the pet is determined as in an instable emotional status; and the brainwave detecting device 110 may proceed to perform brainwave detection for the pet.

In a further embodiment, a distance between each separate characteristic set and the reference characteristic set may be calculated, and when the distance is less than a predetermined threshold, a count is incremented. When the ratio of the count to k is less than a predetermined value, it may be determined that the pet is in a stable emotional status. Otherwise, the pet is in an instable emotional status, and the brainwave detecting device 110 may proceed with the brainwave detection for the pet. Herein, the distance between each separate brainwave characteristic set and the reference characteristic set may be, for example, a Euclidean distance.

Step S230: determining when the brain waves match a first emotional status of a plurality of emotional statuses in an emotion template. When so, go to the step S240. If not, go to the step S250.

It is to be understood that there may be an emotion template stored in the memory 121 in the computing device 120 in some embodiments. A plurality of emotional statuses are recorded in the emotion template, and each emotional status corresponds to a plurality of characteristic values (or a characteristic set), respectively. In some embodiments, those emotional statuses may comprise a happy mood, an angry mood, a sad mood, and etc., but the subject matter is not limited as such. In some embodiments, those emotional statuses may comprise a combined status of multiple types of moods described above, and each combined status of the multiple types of moods may respectively correspond to one characteristic set.

In some embodiments, after the processor 122 determines that the brain wave signals are approximately in the stable status based on the above described method, the processor 122 will compare those characteristic values with the emotion template. In other words, the processor 122 may determine whether those characteristic values match at least one emotional status in the emotion template. If so, the step S240 is performed. If not, the step S250 is performed. It is to be understood that the emotional statuses in the emotion template may correspond to the frequency ranges of the brain wave signals as described above to a considerable extent, but the subject matter is not limited as such.

In some embodiments, the processor 122 may calculate a difference or distance between the brain waves reference characteristic set in the stable state and the brain waves characteristic set associated with any one emotional status in the emotion template, in order to determine whether the reference characteristic set of those brain waves match the characteristic set associated with any one emotion in the emotion template.

In some embodiments, the reference characteristic set is not required to be exactly identical to the characteristic sets associated with the emotional statuses in the emotion template, and as long as the difference or distance between characteristic values and the characteristic set associated with at least one emotional status in the emotion template is less than a predetermined value, the processor 122 may determine that the pet or the brain waves match one emotional status (the first emotional status, for example) in the emotion template.

S240: outputting information regarding the pet being in the first emotional status.

In some embodiments, when the characteristic values match the characteristic set which some emotion in the emotion template corresponds to, the processor 122 may determine the pet is associated with the emotion. For example, when those characteristic values match the characteristic set which the happy emotion in the emotion template corresponds to, the processor 122 may then determine that the pet corresponds to the happy emotion.

Step S250: updating the emotion template in accordance with a confirmation operation and the characteristic values.

In some embodiments, when those characteristic values or the characteristic set do not match any of the reference characteristic sets which the emotions in the emotion template correspond to, the processor 122 may determine that the current emotion associated with the pet is not recorded in the emotion template. Under such situation, the processor 122 may create another emotion in the emotion template based on those characteristic values.

In some embodiments, the processor 122 may use the reference characteristic set for brain waves in the stable state as the brainwave reference characteristic set which the newly created emotion corresponds to.

In some embodiments, when those characteristic values do not match any of the characteristic values to which the emotions in the emotion template corresponds to, the processor 122 may send an inquiry message via the output/input device 130 to notify the user. For example, the inquiry message displayed at the output/input device 130 may show contents such as "the current brain wave signals correspond to some emotional status not recorded in the emotion template; please confirm whether an emotional status is to be created," for the user of the emotion detection system 100 to confirm. In some embodiments, there are multiple options included in the inquiry message for the user of the emotion detection system 100 to select.

In some embodiments, the user may input a confirmation operation to the inquiry message by the output/input device 130. When the processor 122 receives a message corresponding to the confirmation operation, the processor 122 may create an emotional status in the emotion template based on those characteristic values or the reference characteristic set.

In some embodiments, the confirmation operation which the user of the emotion detection system 100 performs by the output/input device 130 further comprises a name of the emotional status to be created, such as names like "calm status" and etc. It is to be understood that the confirmation operation described above may provide the user of the emotion detection system 100 with an opportunity to customize the emotions to be created.

Simply speaking, when the characteristic values of the brain wave signals or the reference characteristic set correspond to some emotion in the emotion template, the processor 122 may transmit messages corresponding to the emotion to the output/input device 130 to present the messages corresponding to that emotion to the user of the emotion detection system 100. By this, the user of the emotion detection system 100 may understand the current emotional status of the pet. For example, when the processor 122 determines that the characteristic values of the brain wave signals correspond to the happy mood in the emotion template, the information regarding the pet being in a happy mood may be displayed at the output/input device 130. When the current emotion of the pet is determined as not matching any emotional status in the emotion template, the user may be provided with the option to create the current emotion of the pet. More accurate and customized emotion templates for each different pet may be provided thereby, and further each owner of the pets may understand the current emotion of the pets more easily.

In some embodiments, the processor 122 and the output/input device 130 may co-operate to provide further information. For example, in addition to showing that the pet is in a happy mood, the output/input device 130 may activate its photo or video capability to capture a photo or a video of the pet, and the processor 122 may store the picture or the video in the memory 121. When the processor 122 determines that the characteristic values of the brain wave signals correspond to the happy mood again thereafter, the processor 122 may transmit the picture or the video altogether to the output/input device 130 to cause the output/input device 130 to provide other information related to the happy mood. It should be appreciated, however, that the subject matter of the present application is not limited as such.

In some embodiments, the processor 122 may display a representation with multiple axes by the output/input device 130 so as to show the emotion of the pet. For example, the representation with multiple axes may comprise the plurality of emotional statuses described above, e.g., being happy, being tired, playful, feeling unfamiliar, and etc. In some embodiments, the processor 122 may reflect the combined emotional status by the representation with multiple axes, for example 30% sleepy, 50% feeling unfamiliar and 20% tired, and etc. It is to be understood, however, that the subject matter of the present application is not limited as such.

In some embodiments, the computing device 120 in the emotion detection system 100 may act as a stand-alone emotion detecting device, e.g., a cloud server. In such a case, it may co-operate with the brainwave detecting device 110 and the output/input device 130 to implement the above-described method 200 for emotion detection.

In some embodiments, the computing device 120 and the output/input device 130 in the emotion detection system 100 belong to the same device, e.g., a smart phone. In such a case, the method for emotion detection 200 may be associated with an application running on the smart phone to implement the method 200 for emotion detection described above.

It may be learnt from the implementations of the present application described above that an emotion detecting device, a system and a method for emotion detection are provided by the present application; the emotion of the pet may be determined based on an emotion template, and emotions which are not defined in the emotion template may be created for users to determine the emotion of the pet efficiently and conveniently. The relationships with the pets are improved and excellent experience is provisioned to the user.

Although the present application has been described above by embodiments thereof, the present application is not limited in those embodiments. Any one skilled in the art can make various modifications and variations to the embodiments without departing from the scope or spirit of the present application. Therefore, it is intended that the protection scope of the present application is defined by the following claims.

What is claimed is:

1. An emotion detecting device, comprising:
a memory storing an emotion template with a plurality of emotional statuses;
a processor electrically coupled to the memory, the processor receiving a plurality of characteristic values transformed from a plurality of brain waves of a pet during a period, and determining whether the brain waves correspond to a stable state based on variation of the characteristic values during the period, wherein the brain waves are obtained by detection via a brainwave detecting device; and
an output/input device electrically coupled to the processor;
wherein, when the brain waves correspond to the stable state, the processor determines whether the brain waves match a first emotional status of the plurality of emotional statuses, and when the brain waves match the first emotional status, information regarding the pet being in the first emotional status is output at the output/input device;
wherein, when the brain waves do not match at least one of the plurality of emotional statuses, the processor updates the emotion template in accordance with a confirmation operation and the plurality of characteristic values,
wherein the processor transforms the brain waves during the period to a number K of characteristic sets,
wherein each of the brain waves corresponding to a number N of frequencies based on a transform algorithm, wherein frequency data items for the number N of frequencies are the characteristic values, and each of the number K of characteristic sets includes the frequency data items for the number N of frequencies;
the processor, based on the number K of frequency data items for each frequency among the number K of characteristic sets during the period, computing a median of the number K of frequency data items corresponding to the number N of frequencies, and generating a reference characteristic set of the period, wherein the reference characteristic set includes the number N of the medians calculated from the number K of characteristic sets, and each of the number N of the medians corresponds to one of the number N of frequencies;
wherein the processor calculates a frequency data difference between the frequency data items for the number N of frequencies of each of the number K of characteristic sets and the number N of the medians of the reference characteristic set,
wherein when the frequency data difference is less than a predetermined threshold, a count is incremented, and the brain waves are determined as in the stable state when the count in the period is larger than a predetermined parameter.

2. The emotion detecting device of claim 1, wherein, when the brain waves do not match at least one of the plurality of emotional statuses, the processor creates a second emotional status in the emotion template based on the characteristic values and the confirmation operation received from the output/input device.

3. The emotion detecting device of claim 1, wherein the processor transforms the brain waves to the characteristic values based on a transform algorithm comprising a fast Fourier transform algorithm or a wavelet transform algorithm.

4. The emotion detecting device of claim 1, wherein the brain waves are determined as in the stable state when the frequency data differences are less than a predetermined threshold.

5. An emotion detection system, comprising:
a brainwave detecting device for detecting a plurality of brain waves of a pet during a period;
a computing device electrically coupled to the brainwave detecting device, the computing device transforming the plurality of brain waves to a plurality of characteristic values and determining whether the brain waves correspond to a stable state based on variation of the characteristic values during the period;
wherein, when the brain waves correspond to the stable state, the computing device determines whether the brain waves match a first emotional status among a plurality of emotional statuses of an emotion template;
wherein, when the brain waves match the first emotional status, the pet is determined as in the first emotional status,
when the brain waves do not match at least one of the plurality of emotional statuses, the computing device updates the emotion template in accordance with a confirmation operation and the plurality of characteristic values; and
an output/input device electrically coupled to the computing device, the output/input device outputting information regarding the pet being in the first emotional status when the brain waves match the first emotional status,
wherein the computing device transforms the brain waves during the period to a number K of characteristic sets,
wherein each of the brain waves corresponding to a number N of frequencies based on a transform algorithm, wherein frequency data items for the number N of frequencies are the characteristic values, and each of the number K of characteristic sets includes the frequency data items for the number N of frequencies;
the processor, based on the number K of frequency data items for each frequency among the number K of characteristic sets during the period, computing a median of the number K of frequency data items corresponding to the number N of frequencies, and generating a reference characteristic set of the period, wherein the reference characteristic set includes the number N of the medians calculated from the number K of characteristic sets, and each of the number N of the medians corresponds to one of the number N of frequencies;
wherein the computing device calculates a frequency data difference between the frequency data items for the number N of frequencies of each of the number K of characteristic sets and the number N of the medians of the reference characteristic set,
wherein when the frequency data difference is less than a predetermined threshold, a count is incremented, and the brain waves are determined as in the stable state when the count in the period is larger than a predetermined parameter.

6. The emotion detection system of claim 5, wherein, when the brain waves do not match at least one of the plurality of emotional statuses, the computing device creates a second emotional status in the emotion template based on the characteristic values and the confirmation operation received from the output/input device.

7. The emotion detection system of claim 5,
wherein, when the frequency data differences are less than a predetermined threshold, the brain waves are determined as in the stable state.

8. A method for emotion detection, comprising:
receiving a plurality of characteristic values transformed from a plurality of brain waves of a pet during a period, wherein the brain waves are obtained by detection via a brainwave detecting device;
determining whether the brain waves correspond to a stable state based on variation of the characteristic values during the period, further comprising:
transforming the brain waves during the period to a number K of characteristic sets, wherein each of the brain waves corresponding to a number N of frequencies based on a transform algorithm, wherein frequency data items for the number N of frequencies are the characteristic values, and each of the number K of characteristic sets includes the frequency data items for the number N of frequencies;
based on the number K of frequency data items for each frequency among the number K of characteristic sets during the period, computing a median of the number K of frequency data items corresponding to the number N of frequencies, and generating a reference characteristic set of the period, wherein the reference characteristic set includes the number N of the medians calculated from the number K of characteristic sets, and each of the number N of the medians corresponds to one of the number N of frequencies;
computing a frequency data difference between the frequency data items for the number N of frequencies of each of the number K of characteristic sets and the number N of the medians of the reference characteristic set; and
increasing a count when the frequency data difference is less than a predetermined threshold, wherein the brain waves are determined as in the stable state when the count in the period is larger than a predetermined parameter;
wherein when the brain waves are determined as corresponding to the stable state, determining whether the brain waves match a first emotional status among a plurality of emotional statuses of an emotion template;
when the brain waves match the first emotional status, outputting information regarding the pet being in the first emotional status; and
when the brain waves do not match at least one of the plurality of emotional statuses, updating the emotion template in accordance with a confirmation operation and the plurality of characteristic values.

9. The method for emotion detection of claim 8, further comprising:
when the brain waves do not match at least one of the plurality of emotional statuses, receiving the confirmation operation from an output/input device and creating a second emotional status in the emotion template based on the characteristic values.

10. The method for emotion detection of claim 8,
when the frequency data differences are less than a predetermined threshold, determining the brain waves as in the stable state.

* * * * *